United States Patent [19]
Andersson

[11] Patent Number: 5,616,833
[45] Date of Patent: Apr. 1, 1997

[54] DYNAMIC CONE PENETRATION DEVICE

[76] Inventor: Lars G. A. Andersson, 2172 West 14th Avenue, Vancouver, British Columbia, Canada, V6K 2V7

[21] Appl. No.: 667,391

[22] Filed: Jun. 21, 1996

Related U.S. Application Data

[62] Division of Ser. No. 422,041, Apr. 13, 1995.

[51] Int. Cl.[6] ................................................. G01N 3/00
[52] U.S. Cl. .................................................... 73/84
[58] Field of Search ............................. 73/12.01, 81, 82, 73/84, 784; 175/135, 170, 189, 195; 173/105, 148, 211

[56] References Cited

U.S. PATENT DOCUMENTS

| | | | |
|---|---|---|---|
| 2,607,218 | 8/1952 | Hansen | 73/84 |
| 2,716,884 | 9/1955 | Rosenberg | 73/12 |
| 2,833,120 | 5/1958 | Barret et al. | 61/73 |
| 3,946,598 | 3/1976 | Towne et al. | 73/67.1 |
| 4,499,954 | 2/1985 | Diggle | 175/21 |
| 5,313,825 | 5/1994 | Webster et al. | 73/81 |
| 5,319,959 | 6/1994 | Cooper et al. | 73/84 |

*Primary Examiner*—Robert Raevis
*Attorney, Agent, or Firm*—Christensen O'Connor Johnson & Kindness PLLC

[57] ABSTRACT

A dynamic cone penetration device for determining denseness of soil has reduced friction to provide more accurate testing. The device comprises a cone rod having a soil penetrating cone at one end and an anvil at the other end. The cone has a larger diameter than the cone rod, and the anvil has a striking surface for striking with a predetermined force. A rotation system containing a motor rotates the cone rod at a sufficient speed to reduce friction between the cone rod and the soil as the striking surface is struck.

8 Claims, 2 Drawing Sheets

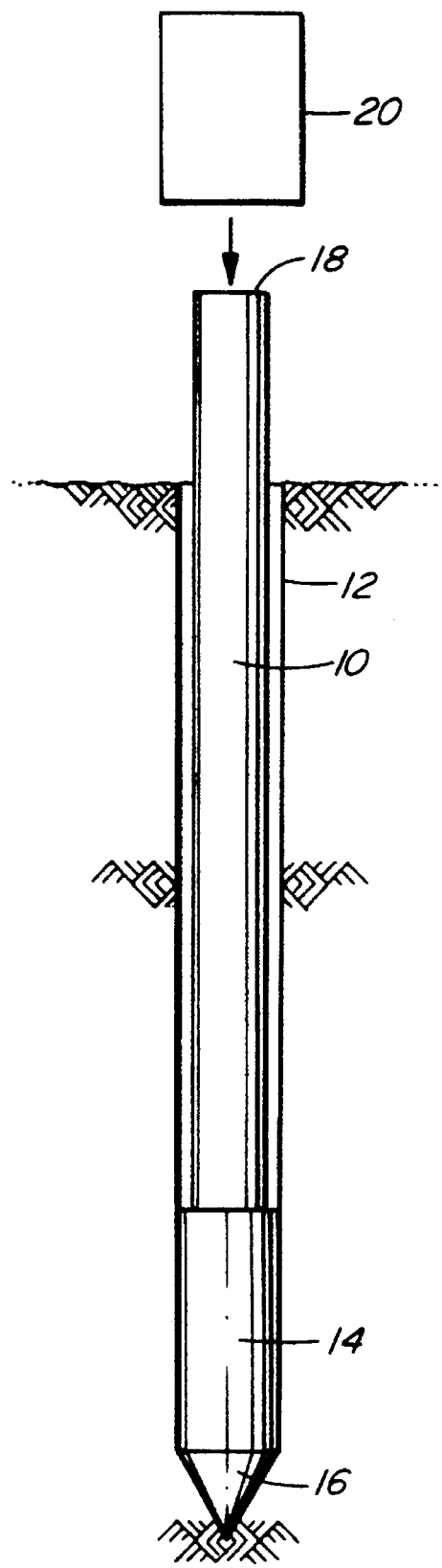
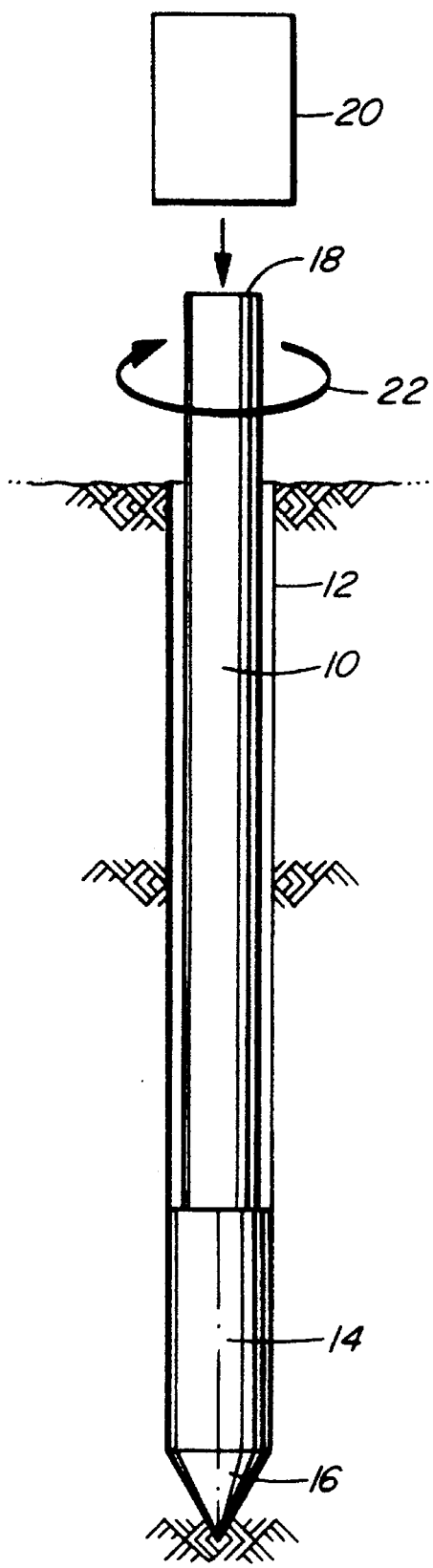
FIG. 1 PRIOR ART
FIG. 2

DYNAMIC CONE PENETRATION DEVICE

This is a divisional of the prior application Ser. No. 08/422,041, filed Apr. 13, 1995, the benefit of the filing date of which is hereby claimed under 35 U.S.C. §120.

TECHNICAL FIELD

The present invention relates to a device for determining the denseness of soil and more specifically for dynamic cone penetration testing devices with reduced friction.

BACKGROUND ART

In geotechnical engineering, it is often necessary to determine the denseness of soil, generally sandy soils, in order to determine permissible loads, possible settlements, earthquake liquifaction potential, densification control, etc. One of the methods used to determine soil density is dynamic cone penetration testing. In this test a fixed weight is dropped for a predetermined distance onto a striking surface of a cone rod which has a penetrating cone at the bottom tip inserted into the soil. The number of blows required to advance the penetrating cone for a predetermined depth into the soil becomes an index of the denseness of the soil. The number of blows generally runs between about 5 and 75 blows per foot of depth. For different soils blow counts can vary from 1 to as high as about 200 for one foot of depth.

In the past friction along the cone rod is reduced by having a cone at the penetrating tip with a larger diameter than the cone rod. This reduces the friction and the method has been proved successful because it is fast, simple and reasonably reliable at shallow depths.

As the depth of soil becomes greater and one is determining density at greater depths, then friction starts to build up between the soil and the rod so that the blows from the drop hammer on the striking surface of the rod no longer reflect the same force on the penetrating tip and thus the number of blows per foot does not have the same meaning because friction has introduced a restriction.

Webster in U.S. Pat. No. 5,313,825 illustrates a penetrometer of the type known in the prior art having a hammer and a penetrating tip at the bottom end of a rod. Diggle in U.S. Pat. No. 4,499,954 shows a method of lubricating a string of hollow rods for a cone penetrometer to attempt to overcome friction between the rod and the soil within the probe hole.

It is an aim of the present invention to reduce the rod friction as the penetrating cone is being driven into the soil so that the number of blows per foot of depth becomes a substantially accurate index whether the test occurs in a shallow or deep probe hole.

This aim of the present invention is achieved by rotating or spinning the rod during the driving advancement. This spinning action is achieved by means of a fixed position motor rotating the cone rod as it is being driven into the soil.

DISCLOSURE OF INVENTION

The present invention provides a dynamic cone penetration device for testing soil comprising a cone rod having a soil penetrating cone at one end and an anvil at the other end, the cone having a larger diameter than the cone rod, the anvil having a striking surface for striking with a predetermined force, and rotating means for rotating the cone rod at a sufficient speed to reduce friction between the cone rod and the soil as the striking surface is struck.

In another embodiment there is provided in a method of measuring soil denseness wherein a penetrating cone at one end of a cone rod is driven a predetermined distance into the soil by counting the number of strikes of a predetermined force on a striking surface of the cone rod, the improvement of reducing soil friction between the cone rod and the soil, comprising the steps of rotating the cone rod at a sufficient speed to reduce friction between the cone rod and the soil while the cone is driven the predetermined distance into the soil.

BRIEF DESCRIPTION OF DRAWINGS

In drawings which illustrate embodiments of the present invention,

FIG. 1 is a schematic elevational view showing a cone rod with a drop hammer for striking a striking surface as known in the prior art, FIG. 2 is a schematic elevational view, similar to FIG. 1 but showing an arrow indicating rotation of the cone rod according to the present invention.

BEST MODE FOR CARRYING OUT THE INVENTION

Figure 3:
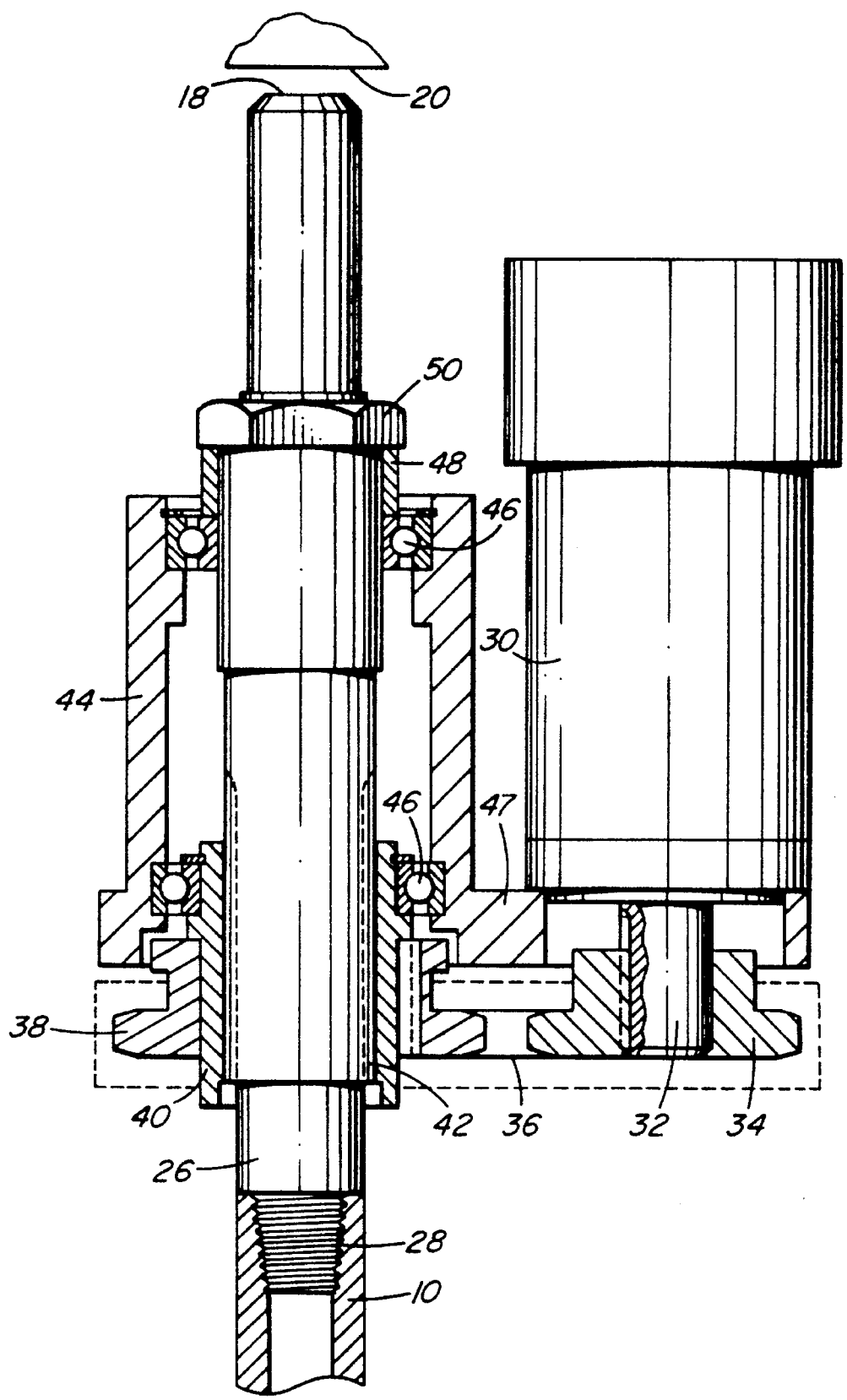
FIG. 3 is a sectional view showing a fixed position motor and chain drive for rotating a cone rod according to one embodiment of the present invention.

A cone rod 10 is illustrated in FIG. 1 positioned in a probe hole 12 in the soil, and having a cone 14 at the base for penetrating the soil. At the top of the cone rod 10 is a striking surface 18 or anvil and a drop hammer 20 is positioned above the striking surface. In operation the drop hammer 20 is raised a predetermined distance and then dropped onto the striking surface 18 forcing the cone 14 into the soil. The number of hammer blows is counted until the cone rod 10 has moved through a distance of one foot and this number of hammer blows represents an index which is related to the density of the soil. FIG. 1 illustrates the dynamic cone penetration test known to the prior art. As stated, one of the problems with this test is that when the probe hole in the soil is deep, the soil can fall inwards against the surface of the cone rod and friction causes a reduction of the striking force to the cone 14. When this happens, the number of hammer blows per foot does not really reflect the true index representing density of the soil.

FIG. 2 illustrates exactly the same penetrating test device as FIG. 1 except that the cone rod 10 is rotated as shown by arrow 22. It has been found that this rotation of the cone rod 10 significantly reduces the friction between the cone rod and the soil.

As shown in FIG. 3, the cone rod 10 has a separate cone rod head 26 attached to the top thereof by a threaded connection 28. Cone rods generally come in 5 foot long lengths, joined by threaded connections, thus permitting the desired testing depth.

A motor 30 is positioned and held so that it cannot rotate and has a motor shaft 32 connected to a drive sprocket 34. A chain drive 36 links the drive sprocket 34 to a driven sprocket 38 fixed to a sleeve 40 which rides on a spline 42 forming part of the cone rod head 26. Transfer of rotation between the cone rod head 26 and the cone rods 10 is achieved by the threaded connections 28 therebetween.

A housing 44, which permits the cone rod head 26 to rotate therein, runs on rails of the mast of a drill rig (not shown) and is thus prevented from rotating. The housing 44 has two antifriction bearings 46 that align the cone rod head 26 with the housing 44, and at the same time allow rotation of the cone rod head 26 in the housing 44. A fixed arm 47 links the motor 30 to the housing 44 and prevents the motor from rotating. Thus, the cone rod head 26 rotates within the fixed housing 44, and the spacing between the chain sprockets 34, 38 remains constant.

A dampener 48, preferably made of elastic material such as rubber or plastic, is positioned adjacent the top bearing 46 between the housing 44 and a nut 50 attached to the top of the cone rod head 26. The dampener 48 dampens the striking force from the hammer 20 being transferred directly to the chain drive 36 and motor 30. Because the driven sprocket 38 is on a spline 42, it moves up and down on the cone rod head 26 representing the flexing movement of the dampener 48. The drive assembly moves down with the cone rod 10 as the cone 14 penetrates into the soil.

The rotational speed of the cone rod is set to suit different soil conditions. It has been found that a rotational speed of from about 10 to 75 rpm generally reduces friction to an insignificant amount. However, in severe friction conditions speeds can be increased and in low friction conditions speeds can be reduced.

The size of the cone 14 is selected for the type of soil under test. For soils such as silt or sand, a cone diameter of about 2 to 2½ inches is sufficient. For larger grain sizes such as gravel a cone diameter of 6 inches is generally required.

Any type of suitable motor may be used such as a gasoline motor, a hydraulic motor, a pneumatic motor or an electric motor. In the case of an electric motor a gearing mechanism may be incorporated between the motor and the drive shaft 32. Whereas a chain mechanism is shown for linking the motor 30 to the cone rod 10, a gearing mechanism may be used or, alternatively, a belt mechanism or other mechanical systems. The important feature is that the cone rod 10 is rotated continuously during the striking action of the hammer 20.

Various changes may be made to the embodiments shown herein without departing from the scope of the present invention which is limited only by the following claims.

The embodiments of the present invention in which an exclusive property or privilege is claimed are defined as follows:

1. In a method of measuring soil denseness wherein a penetrating cone at one end of a cone rod is driven a predetermined distance into the soil by counting the number of strikes of a predetermined force on a striking surface of the cone rod, of a predetermined force, the improvement of reducing soil friction between the cone rod and the soil, comprising the steps of rotating the cone rod at a sufficient speed to reduce friction between the cone rod and the soil while the cone is driven the predetermined distance into the soil.

2. The method of measuring soil denseness according to claim 1 wherein the cone rod is rotated by a motor in a fixed position with a chain drive connecting to the cone rod.

3. The method of measuring soil denseness according to claim 1 wherein the cone rod is rotated at a speed in the range of about 10 to 75 rpm.

4. A method of measuring soil denseness comprising the steps of:

positioning a penetrating cone, located at one end of a cone rod, on soil surface; striking a striking surface on the other end of the cone rod with a predetermined force to penetrate the soil surface;

rotating the cone rod at a sufficient speed to reduce friction between the cone rod and the soil as the penetrating cone penetrates the soil surface; and counting the number of strikes of predetermined force on the striking surface of the cone rod until the penetrating cone has penetrated the soil for a predetermined distance, the number of strikes representing a measurement of soil denseness.

5. The method of measuring soil denseness according to claim 4 wherein the cone rod is rotated by a motor in a fixed position with a chain drive connecting to the cone rod.

6. The method of measuring soil denseness according to claim 5 wherein the cone rod is rotated at a speed in the range of about 10 to 75 rpm.

7. The method of measuring soil denseness according to claim 5 wherein the motor is selected from the group consisting of mechanical, hydraulic, pneumatic and electric.

8. The method of measuring soil denseness according to claim 5 including the step of dampening impact forces on the motor and chain drive when the striking surface of the cone rod is struck.

\* \* \* \* \*